United States Patent [19]

Ungheri et al.

[11] Patent Number: 5,288,704
[45] Date of Patent: Feb. 22, 1994

[54] SYNERGISTIC COMPOSITION COMPRISING A FIBROBLAST GROWTH FACTOR AND A SULFATED POLYSACCHARIDE, FOR USE AS ANTIVIRAL AGENT

[75] Inventors: Domenico Ungheri, Parabiago; Luisa Garofano, Monza; Carlo Battistini, Novate Milanese; Paolo Carminati; Guy Mazué, both of Milan, all of Italy

[73] Assignee: Farmitalia Carlo Erba S.R.L., Milan, Italy

[21] Appl. No.: 830,330

[22] Filed: Jan. 31, 1992

[30] Foreign Application Priority Data

Jan. 31, 1991 [GB] United Kingdom ............ 9102145.1
Jan. 9, 1992 [GB] United Kingdom ............ 9200410.1

[51] Int. Cl.$^5$ ............................................. A61K 37/00
[52] U.S. Cl. ..................................... 514/12; 530/399;
514/54; 514/56; 514/59; 514/885; 514/886;
514/889
[58] Field of Search .................... 514/12, 54, 56, 59,
514/885, 886, 888; 530/399

[56] References Cited

U.S. PATENT DOCUMENTS

| 4,465,666 | 8/1984 | Lukas et al. | 424/145 |
| 4,724,146 | 2/1988 | Kino et al. | 424/89 |
| 4,783,446 | 11/1988 | Neushul | 514/54 |
| 5,110,604 | 5/1992 | Chu et al. | 424/85.2 |
| 5,145,841 | 9/1992 | Cullis-Hill et al. | 514/54 |

FOREIGN PATENT DOCUMENTS

| 0000133 | 1/1979 | European Pat. Off. . |
| 0246753 | 11/1987 | European Pat. Off. . |
| 0251806 | 1/1988 | European Pat. Off. . |
| 0312208 | 4/1989 | European Pat. Off. . |
| 0345660 | 12/1989 | European Pat. Off. . |
| 2245831A | 1/1992 | United Kingdom . |
| WO92/08473 | 5/1992 | World Int. Prop. O. . |
| WO92/13526 | 8/1992 | World Int. Prop. O. . |

OTHER PUBLICATIONS

Science, vol. 248, Jun. 15, 1990, pp. 1410–1413, R. J. Kaner, et al., "Fibroblast Growth Factor Receptor is a Portal of Cellular Entry for Herpes Simplex Virus Type 1".
The Lancet, vol. 1, No. 8546, Jun. 13, 1987, p. 1379, R. Ueno, et al., "Dextran Sulphate, a Potent Anti-HIV Agent In Vitro Having Synergism with Zidovudine".
Proceedings of the National Academy of Sciences of U.S.A., vol. 87, No. 18, Sep. 1990, pp. 6985–6989, M. C. Kiefer, et al., "Ligand-Affinity Cloning and Structure of a Cell Surface Heparan Sulfate Proteoglycan That Binds Basic Fibroblast Growth Factor".
Gospodarowicz et al., "Heparin Protects Basic and Acidic FCF . . . ", Jour. of Cellular Physiology, 128:475–484 (1986).

*Primary Examiner*—Michael G. Wityshyn
*Assistant Examiner*—C. Sayala
*Attorney, Agent, or Firm*—Oblon, Spivak, McClelland, Maier & Neustadt

[57] ABSTRACT

A pharmaceutcial composition is provided for use in the prevention or treatment of viral infections caused by enveloped viruses. The composition comprises a fibroblast growth factor, a sulfated polysaccharide with antiviral activity, and one or more pharmaceutically acceptable carriers. The fibroblast growth factor may be a basic fibroblast growth factor or an analogue thereof, and the polysaccharide may be a carrageenan, heparin, dextran sulfate, pentosan polysulfate or a sulfated polysaccharides produced by marine algae belonging to the class of Rhodophyceae.

14 Claims, 6 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:1:

```
Pro  Ala  Leu  Pro  Glu  Asp  Gly  Gly  Ser  Gly  Ala  Phe  Pro  Pro  Gly  His
1                 5                        10                            15

Phe  Lys  Asp  Pro  Lys  Arg  Leu  Tyr  Cys  Lys  Asn  Gly  Gly  Phe  Phe  Leu
                 20                        25                       30

Arg  Ile  His  Pro  Asp  Gly  Arg  Val  Asp  Gly  Val  Arg  Glu  Lys  Ser  Asp
```

```
                    35                          40                          45

Pro His Ile Lys Leu Gln Leu Gln Ala Glu Glu Arg Gly Val Val Ser
        50                      55                      60

Ile Lys Gly Val Cys Ala Asn Arg Tyr Leu Ala Met Lys Glu Asp Gly
    65                  70                  75                      80

Arg Leu Leu Ala Ser Lys Cys Val Thr Asp Glu Cys Phe Phe Phe Glu
                    85                      90                  95

Arg Leu Glu Ser Asn Asn Tyr Asn Thr Tyr Arg Ser Arg Lys Tyr Ser
                    100                     105                 110

Trp Tyr Val Ala Leu Lys Arg Thr Gly Gln Tyr Lys Leu Gly Ser Lys
                115                     120                 125

Thr Gly Pro Gly Gln Lys Ala Ile Leu Phe Leu Pro Met Ser Ala Lys
        130                     135                     140

Ser
    145
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:2:

```
    Gly Thr Met Ala Ala Gly Ser Ile Thr Thr Leu
    1               5                   10
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:3:

```
    Met Ala Ala Gly Ser Ile Thr Thr Leu
    1               5
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:4:

```
    Ala Ala Gly Ser Ile Thr Thr Leu
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Homo sapiens (xi) SEQUENCE DESCRIPTION: SEQ ID NO:5:

```
Ala  Gly  Ser  Ile  Thr  Thr  Leu
 1                 5
```

(2) INFORMATION FOR SEQ ID NO:6:

(i) SEQUENCE CHARACTERISTICS:
        (A) LENGTH: 140 amino acids
        (B) TYPE: amino acid
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:6:

```
Phe  Asn  Leu  Pro  Pro  Gly  Asn  Tyr  Lys  Lys  Pro  Lys  Leu  Leu  Tyr  Cys
 1                 5                        10                       15

Ser  Asn  Gly  Gly  His  Phe  Leu  Arg  Ile  Leu  Pro  Asp  Gly  Thr  Val  Asp
                20                       25                       30

Gly  Thr  Arg  Asp  Arg  Ser  Asp  Gln  His  Ile  Gln  Leu  Gln  Leu  Ser  Ala
           35                       40                       45

Glu  Ser  Val  Gly  Glu  Val  Tyr  Ile  Lys  Ser  Thr  Glu  Thr  Gly  Gln  Tyr
     50                       55                       60

Leu  Ala  Met  Asp  Thr  Asp  Gly  Leu  Leu  Tyr  Gly  Ser  Gln  Thr  Pro  Asn
65                       70                       75                       80

Glu  Glu  Cys  Leu  Phe  Leu  Glu  Arg  Leu  Glu  Glu  Asn  His  Tyr  Asn  Thr
                85                       90                       95

Tyr  Ile  Ser  Lys  Lys  His  Ala  Glu  Lys  Asn  Trp  Phe  Val  Gly  Leu  Lys
               100                      105                      110

Lys  Asn  Gly  Ser  Cys  Lys  Arg  Gly  Pro  Arg  Thr  His  Tyr  Gly  Gln  Lys
               115                      120                      125

Ala  Ile  Leu  Phe  Leu  Pro  Leu  Pro  Val  Ser  Ser  Asp
           130                      135                      140
```

(2) INFORMATION FOR SEQ ID NO:7:

(i) SEQUENCE CHARACTERISTICS:
        (A) LENGTH: 140 amino acids
        (B) TYPE: amino acid
        (D) TOPOLOGY: linear (ii) MOLECULE TYPE: protein (vi) ORIGINAL SOURCE:
        (A) ORGANISM: Bos taurus (xi) SEQUENCE DESCRIPTION: SEQ ID NO:7:

```
Phe  Asn  Leu  Pro  Leu  Gly  Asn  Tyr  Lys  Lys  Pro  Lys  Leu  Leu  Tyr  Cys
 1                 5                        10                       15
```

-continued

```
Ser Asn Gly Gly Tyr Phe Leu Arg Ile Leu Pro Asp Gly Thr Val Asp
             20                      25                      30

Gly Thr Lys Asp Arg Ser Asp Gln His Ile Gln Leu Gln Leu Cys Ala
         35                  40                  45

Glu Ser Ile Gly Glu Val Tyr Ile Lys Ser Thr Glu Thr Gly Gln Phe
     50                  55                  60

Leu Ala Met Asp Thr Asp Gly Leu Leu Tyr Gly Ser Gln Thr Pro Asn
 65                  70                  75                      80

Glu Glu Cys Leu Phe Leu Glu Arg Leu Glu Glu Asn His Tyr Asn Thr
                 85                  90                      95

Tyr Ile Ser Lys Lys His Ala Glu Lys His Trp Phe Val Gly Leu Lys
             100                 105                 110

Lys Asn Gly Arg Ser Lys Leu Gly Pro Arg Thr His Phe Gly Gln Lys
             115                 120                 125

Ala Ile Leu Phe Leu Pro Leu Pro Val Ser Ser Asp
 130                 135                 140
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
Phe Phe Phe Glu Arg Leu Glu Ser Asn Asn Tyr Asn Thr Tyr Arg Ser
 1               5                  10                      15

Arg Lys Tyr Ser Ser Trp Tyr Val Ala Leu Lys Arg
             20                  25
```

( 2 ) INFORMATION FOR SEQ ID NO:9:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

```
Arg Leu Glu Ser Asn Asn Tyr Asn Thr Tyr Arg Ser Arg Lys Tyr Ser
 1               5                  10                      15

Ser Trp Tyr Val Ala Leu Lys Arg
             20
```

( 2 ) INFORMATION FOR SEQ ID NO:10:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

```
Ser Asn Asn Tyr Asn Thr Tyr Tyr Arg Ser Arg Lys Tyr Ser Ser Trp
 1               5                  10                      15

Tyr Val Ala Leu Lys Arg
```

( 2 ) INFORMATION FOR SEQ ID NO:11:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Tyr Asn Thr Tyr Arg Ser Arg Lys Tyr Ser Ser Trp Tyr Val Ala Leu
1               5                   10                  15

Lys Arg
```

( 2 ) INFORMATION FOR SEQ ID NO:12:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Tyr Asn Thr Tyr Arg Ser Arg Lys Tyr Ser Ser Trp Tyr Val Ala Leu
1               5                   10                  15

Lys Arg Thr Gly Gln Tyr Lys Leu Gly Pro Lys Thr Gly Pro Gly Gln
                20                  25                  30

Lys Ala Ile Leu Phe Leu Pro Met Ser Ala Lys Ser
                35                  40
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Tyr Arg Ser Arg Lys Tyr Ser Ser Trp Tyr
1               5                   10
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:14:

```
Tyr Arg Ser Arg Lys Tyr Ser Ser Trp Tyr Val Ala Leu
1               5                   10
```

( 2 ) INFORMATION FOR SEQ ID NO:15:

( i ) SEQUENCE CHARACTERISTICS:
        ( A ) LENGTH: 15 amino acids
        ( B ) TYPE: amino acid (D) TOPOLOGY: linear (i i) MOLECULE TYPE: peptide (v) FRAGMENT TYPE: internal (x i) SEQUENCE DESCRIPTION: SEQ ID NO:15:

Tyr Arg Ser Arg Lys Tyr Ser Ser Trp Tyr Val Ala Leu Lys Arg
 1               5                  10                  15

SYNERGISTIC COMPOSITION COMPRISING A FIBROBLAST GROWTH FACTOR AND A SULFATED POLYSACCHARIDE, FOR USE AS ANTIVIRAL AGENT

The present invention relates to a synergistic pharmaceutical composition having antiviral activity which comprises a fibroblast growth factor, a sulfated polysaccharide with antiviral activity and any acceptable pharmaceutical excipient or excipients, for the use in the prevention or treatment of viral infections caused by enveloped viruses.

Enveloped viruses are, for example, herpes virus type $\alpha$, e.g., herpes simplex virus (HSV); herpes virus type $\beta$ or $\gamma$, e.g. cytomegalovirus; orthomyxovirus, e.g. influenza virus; paramyxovirus, e.g. human respiratory syncytial virus (HRSV); tropical viruses responsible for exanthematous fevers and/or encephalitis, e.g. Semliki Forest Virus (SFV), or other tropical deseases, belonging e.g., to the "Toga" and "Arena", groups of viruses; or retrovirus, e.g. the HIV virus responsible for the acquired immuno deficiency syndrome and the MSV virus responsible for the Moloney Sarcoma virus.

A fibroblast growth factor according to the invention may be either a basic fibroblast growth factor or an acidic fibroblast growth factor, or their analogs.

A sulfated polysaccharide with antiviral activity according to the invention may be, e.g., one selected from the group consisting of a carragenan, e.g. $\gamma$ carrageenan, heparin, dextran sulfate, pentosan polysulfate mannane sulfate, dermatan sulfate, heparin super-sulfated, dermatan super-sulfated and agarose-type sulfated polysaccharides e.g. produced by marine algae belonging to the class of Rhodophyceal.

Although much effort has been made to fight the infections caused by the enveloped viruses no really effective drug has yet been identified.

FGF is known as a promoter of angiogenesis, wound healing, tissues regeneration, including bone and nerve tissues. Kaner et al.(Science 248, 1410, 1990) demonstrated that the b-FGF receptor is a portal of cellular entry for HSV type 1. Inhibitors of b-FGF binding to its receptor and competitive antagonists of b-FGF prevent HSV-1 uptake.

We also showed that b-FGF prevents the growth and infectivity of other viruses like herpes simplex type 2 (HSV-2), respiratory syncytial virus (HRSV), Semliki forest virus (SFV), human immunodeficiency virus (HIV) and Moloney sarcoma virus (MSV) (our copending Italian patent application No. 22804A/89).

Sulfated polysaccharides are known to be potent and selective inhibitors of various enveloped viruses (Antiviral Research 9, 335-343, 1988; ibidem 233-246, 1989; ibidem, 12, 1-20, 1989; Antimicrobial Ag. and Chemioth. 31, 1524-1528, 1987; ibidem 31, 1388-1393, 1987; 32, 1742-1745, 1988; Science 240, 646-653, 1988; The Lancet, Jun. 13, 1979-1982, 1987; Virology 164, 542-546, 1988).

We have surprisingly found that combining a fibroblast growth factor and a sulfated polysaccharide, the obtained antiviral activity is superior to that expected from the sum of the antiviral activities of the individual constituents of the combination, thus indicating the presence of a synergistic effect. The combination of the two components is therefore more effective in the treatment of the viral infections.

Figure 1:
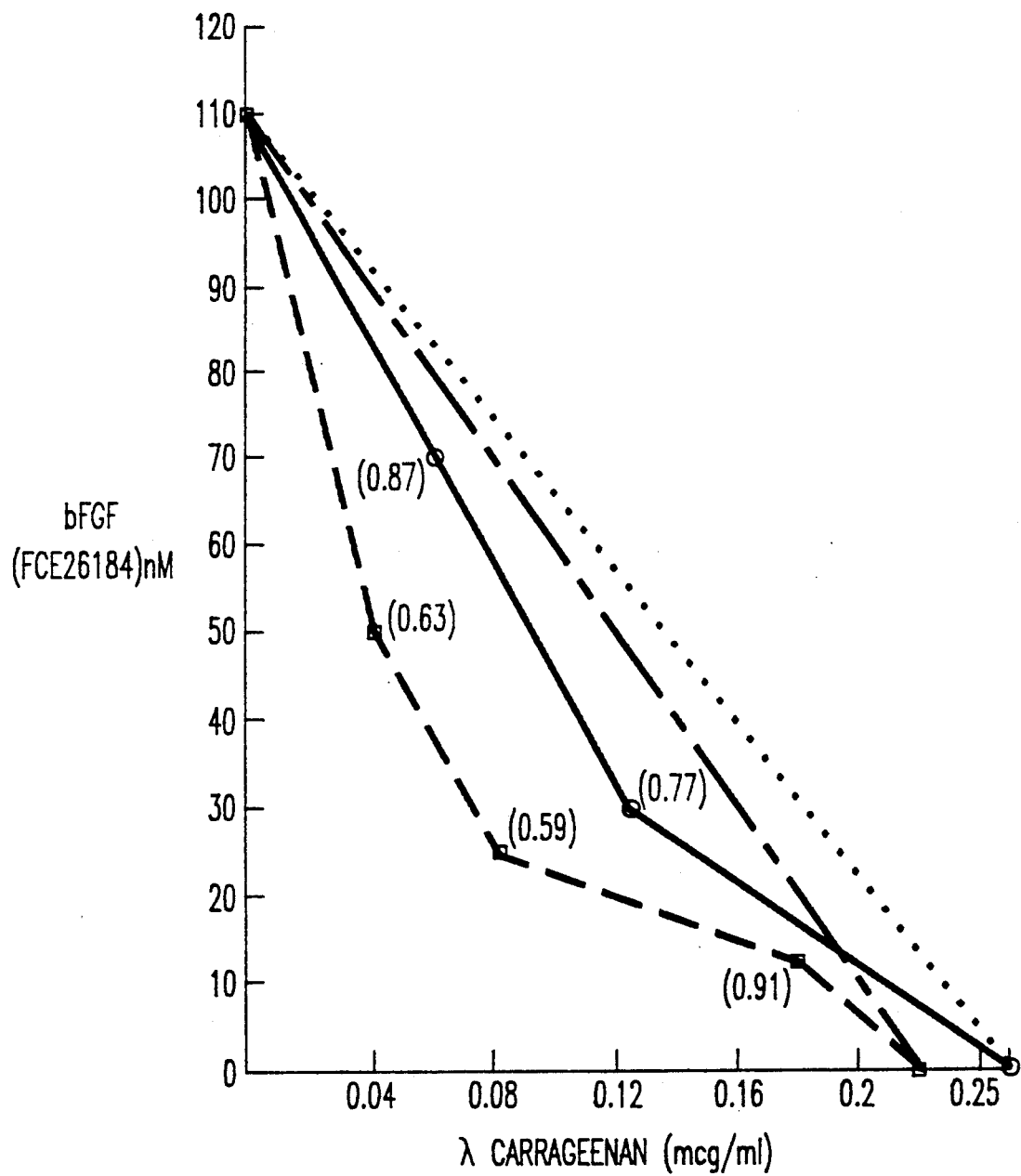
FIG. 1 shows the in vitro effect of various combination of $\lambda$ carrageenan and bFGF against HSV-1.

The present invention relates to a synergistic pharmaceutical composition having antiviral activity which comprises a fibroblast growth factor, a sulfated polysaccharide with antiviral activity and any acceptable pharmaceutical excipient or excipients, for use in the prevention or treatment of viral infections caused by enveloped viruses.

The invention further concerns a process for preparing the above mentioned composition, comprising the step of combining a fibroblast growth factor, and a sulfated polysaccharide in a pharmaceutically acceptable excipient or excipients.

In particular, the invention refers to the prevention and treatment, by use of a composition according to the invention of infections caused by alpha type herpes viruses such as, e.g., herpes simplex virus (HSV), in particular HSV-1 and HSV-2, and herpes varicella/-zoster; beta or gamma type herpes viruses, e.g. cytomegalovirus; orthomyxovirus, e.g. influenza virus, paramyxovirus, e.g. human respiratory syncytial virus (HRSV); tropical viruses responsible for exanthematous fevers and/or encephalitis, e.g. Semliki Forest virus (SFV) or other tropical diseases, belonging, e.g., to the "Toga" and "Arena" groups of viruses; or retroviruses, e.g. the HIV virus responsible for the acquired immune deficiency syndrome and the MSV virus responsible for the Monoley Sarcoma virus.

Particular examples of viruses towards which the pharmaceutical composition according to the invention have proved to be effective are, e.g., the herpes simplex viruses (HSV), in particular HSV-1 and HSV-2.

A fibroblast growth factor (FGF) according to the invention can be either basic FGF (bFGF), human or bovine, or acidic FGF (aFGF), human or bovine, or an analogue of the aforesaid bFGF and aFGF.

The aforementioned growth factors, namely human and bovine bFGF and human or bovine aFGF, are known factors, which are described for example in the published international patent applications PCT W086/07595 and PCT W087/01728, and in the published European patent applications No. 226181, No. 237966 and No. 259953, as well as in various scientific articles such as for example, Science vol. 233, , pp. 545-548, Aug. 1, 1986; Embo Journal Vol. 5, No. 10, pp.2523-2528, 1986;

Biochemical and Biophysical Res. Communications vol. 140, No. 3, pp. 874-880, 1986; Biochemical and Biophysical Res. Communications vol. 133, No. 2, pp. 554-562, 1985; Science vol. 230, pp. 1385-1388, Dec. 20, 1985.

Human bFGF is a polypeptide with 146 aminoacids, having the sequence shown hereunder (SEQ ID NO: 1):

```
  1                                          10
Pro Ala Leu Pro Glu Asp Gly Gly Ser Gly Ala Phe Pro Gly His 20                                 30
Phe Lys Asp Pro Lys Arg Leu Tyr Cys Lys Asn Gly Gly Phe Phe Leu

40
Arg Ile His Pro Asp Gly Arg Val Asp Gly Val Arg Glu Lys Ser Asp 50                                 60
Pro His Ile Lys Leu Gln Leu Gln Ala Glu Glu Arg Gly Val Val Ser 70                                 80
Ile Lys Gly Val Cys Ala Asn Arg Tyr Leu Ala Met Lys Glu Asp Gly

90
Arg Leu Leu Ala Ser Lys Cys Val Thr Asp Glu Cys Phe Phe Phe Glu 100                                110
Arg Leu Glu Ser Asn Asn Tyr Asn Thr Tyr Arg Ser Arg Lys Tyr

120
Ser Trp Tyr Val Ala Leu Lys Arg Thr Gly Gln Tyr Lys Leu Gly Ser 130                           140
Lys Thr Gly Pro Gly Gln Lys Ala Ile Leu Phe Leu Pro Met Ser Ala

146
Lys Ser
```

Bovine bFGF differs only in position 112, where threonine is substituted by serine, and in position 128 where serine is substited by proline.

The molecule of human bFGF, as well as of bovine bFGF, can have an N-terminal extension that can contain all or part of the sequence of the following 11 aminoacids (SEQ NO ID: 2):

(i) Gly-Thr-Met-Ala-Ala-Gly-Ser-Ile-Thr-Thr-Leu, for example, in particular, the following 9 aminoacids (SEQ ID NO: 3)

(ii) Met-Ala-Ala-Gly-Ser-Ile-Thr-Thr-Leu, or the following 8 aminoacids (SEQ ID NO: 4)

(iii) Ala-Ala-Gly-Ser-Ile-Thr-Thr-Leu, or the following 7 aminoacids (SEQ ID NO: 5)

(iv) Ala-Gly-Ser-Ile-Thr-Thr-Leu.

The molecules of 146 aminoacids of human and bovine bFGF can also be lacking in one or more aminoacid residues at the N-terminal.

Human aFGF is a polypeptide with 140 aminoacids, having the sequence shown hereunder (SEQ ID NO: 6)

```
  1                                          10
Phe Asn Leu Pro Pro Gly Asn Tyr Lys Lys Pro Lys Leu Leu Tyr Cys 20                                 30
Ser Asn Gly Gly His Phe Leu Arg Ile Leu Pro Asp Gly Thr Val Asp

40
Gly Thr Arg Asp Arg Ser Asp Gln His Ile Gln Leu Gln Leu Ser Ala 50                                 60
Glu Ser Val Gly Glu Val Tyr Ile Lys Ser Thr Glu Thr Gly Gln Tyr 70                         80
Leu Ala Met Asp Thr Asp Gly Leu Leu Tyr Gly Ser Gln Thr Pro Asn

90
Glu Glu Cys Leu Phe Leu Glu Arg Leu Glu Glu Asn His Tyr Asn Thr 100                           110
Tyr Ile Ser Lys Lys His Ala Glu Lys Asn Trp Phe Val Gly Leu Lys

120
Lys Asn Gly Ser Cys Lys Arg Gly Pro Arg Thr His Tyr Gly Gln Lys 130                           140
Ala Ile Leu Phe Leu Pro Leu Pro Val Ser Ser Asp
```

Bovine aFGF is also a polypeptide with 140 aminoacids, having the sequence shown hereunder (SEQ ID NO: 7) and characterized by a high degree of homology with that of human aFGF,

```
  1                                          10
Phe Asn Leu Pro Leu Gly Asn Tyr Lys Lys Pro Lys Leu Leu Tyr Cys
```

```
                           20                        30
Ser Asn Gly Gly Tyr Phe Leu Arg Ile Leu Pro Asp Gly Thr Val Asp

40
Gly Thr Lys Asp Arg Ser Asp Gln His Ile Gln Leu Gln Leu Cys Ala 50                              60
Glu Ser Ile Gly Glu Val Tyr Ile Lys Ser Thr Glu Thr Gly Gln Phe 70                              80
Leu Ala Met Asp Thr Asp Gly Leu Leu Tyr Gly Ser Gln Thr Pro Asn

90
Glu Glu Cys Leu Phe Leu Glu Arg Leu Glu Glu Asn His Tyr Asn Thr 100                                     110
Tyr Ile Ser Lys Lys His Ala Glu Lys His Trp Phe Val Gly Leu Lys

120
Lys Asn Gly Arg Ser Lys Leu Gly Pro Arg Thr His Phe Gly Gln Lys 130                         140
Ala Ile Leu Phe Leu Pro Leu Pro Val Ser Ser Asp
```

The molecules of both human and bovine aFGF can also have the same extensions and deletions at the N-terminal indicated above with reference to bFGF molecules. The fibroblast growth factors according to the invention can also be amidated at the C-terminal.

An analogue of the aforementioned fibroblast growth factors can be, for example, according to the invention, any fragment, even in amidated form, of the entire FGF molecule, which retains its capacity to bind to the receptor.

Examples of such fragments are described in the published European patent application No. 246.753. They may be, for example, in particular, the polypeptides composed of the aminoacid sequences 93–120; 97–120; 100–120; 103–120; 103–146; 106–115; 106–118; 106–120; 106–125; 106–130; 106–135; 106–140; 106–146 and 107–110 of both human and bovine bFGF, both in free form and in amidated form.

An analogue of the fibroblast growth factor of the invention can be a mutein deriving from the aforementioned FGF polypeptides or their analogues, both in amidated and non-amidated form, by replacement and/or deletion of one or more aminoacids, which retains equivalent properties, in particular an equivalent capacity to bind itself to the FGF receptor. Thus, for example, the aminoacid in position 112 can be either Thr or Ser; the aminoacid in position 128 can be either Ser or Pro; the aminoacid in position 113 can be either Ala or Ser; the aminoacid in position 114 can be either Met or Trp and the aminoacid in position 115 can be either Phe or Tyr.

Mixtures of different forms of FGF, for example, of the forms referred to previously which derive from different types of extensions or deletions at the N-terminal, are also to be considered as being within the scope of this invention. The term "fibroblast growth factor" as used herein refers also to such mixtures, as well as to all the analogues indicated above.

As mentioned previously, the growth factors used according to the invention are known factors and can therefore be prepared by known methods, for example by recombinant DNA techniques, e.g. by procedures similar to those described in the published international patent applications PCT W086/07595 and PCT W087/01728 and in the published European patent applications No. 226181, No. 237966 and No. 259953, mentioned previously. Known techniques may also be used to obtain the FGF analogues, e.g. the fragments of FGF of the invention. For example, it is possible to use procedures similar to those described in the aforesaid published European patent application No. 246753 and in the references mentioned therein, for example by means of solid phase synthesis as described in JACS 85, pg.2149 (1963). Chemical synthesis is preferred for fragments composed of short aminoacid sequences, e.g. sequences shorter than 40 aminoacids, whereas preparation by recombinant DNA is preferred, for example, for preparing native FGF molecules or their analogues containing, e.g., more than 40 aminoacids.

The sulfated polysaccharide with antiviral activity component of the compositions of the invention may be, e.g., selected from the group consisting of a carrageenan, heparin, dextran sulfate, pentosan polysulfate, mannane sulfate, dermatan sulfate, heparin super-sulfated, dermatan super-sulfated and an agarose-type sulfated polysaccharide produced by marine algae belonging to the class of Rhodophyceae (red algae). The agarose-type sulfated polysaccharides produced by red algae, according to the invention (hereinafter designed as ASP) have a common backbone of the agaroid-type, composed of alternating $\beta(1\rightarrow4)$D-galactose and $\alpha(1\rightarrow3)$L-galactose repeating units. In particular, after being purified to homogeneity by anion exchange chromatography by application of an increasing sodium chloride gradient, dialysed exhaustively against distilled water, and freeze-dried, they have the following properties:

(a) elementary analysis : 20–35% carbon, 3.2–5.5% hydrogen, less than 1% nitrogen and more than 8% sulphur, when calculated as anhydrous compound;

(b) molecular weight of up to 10000 kDA as measured by high performance size exclusion chromatography;

(c) soluble in water, in aqueous phosphate buffers at pH 1 to 13, and in aqueous solvents containing up to 20% water-soluble alcohols, but insoluble in benzene, chloroform, ethyl ether, and in aqueous-alcoholics solutions containing more than 80% methyl- or ethyl-alcohol and 1 g/l of sodium chloride;

(d) soluble in water in the presence of barium chloride, but after being hydrolysed for 3 hrs at 120° C. in aqueous 2M hydrochloric acid, it gives a precipitate of barium sulphate upon addition of barium chloride;

(e) galactose, 3,6-anhydrogalactose and all their derivatives carrying one to three substituents selected from the group of sulfate hemiester, methyl ether, pyruvate (1-carboxyethylidene groups and a sugar residue like galactose or xylose, together accounts for more than 90% of the total monosaccharidic units;

(f) more than 30% of the total monosaccharidic units consists of 4-0-linked α-L-galactopyranosidic residues which can carry substituents as under (e) above at positions 2, 3 and 6;

(g) more than 40% of the total monosaccharidic units consists of 3-0-linked β-D-galactopyranosidic residues which can carry substituents as under (e) above at positions 2, 4 and 6;

(h) more than 40% of the total monosaccharidic units consist of 4-0-linked α-L-galactopyranosidic residues which can carry substituents as under (e) above at positions 2,3 and 6, plus 4-0-linked 3,6-anhydro-α-L-galactopyranosidic residues which can carry substituents as under (e) above at position 2;

(i) pyruvate (1-carboxyethylidene) groups linked as cyclic ketals bridging 0-4 and 0-6 of β-D-galactopyranosidic residues occur as substituents in less than 10% of the total monosaccharidic units;

(j) the molar ratio of methyl ether group substituents per monosaccharidic unit do not exceed 0.3:1;

(k) sulphate hemiester groups can be present at positions 2, 4 and 6 of the β-D-galactopyranosidic residues, at positions 2,3 and 6 of the α-L-galactopyranosidic residues and at position 2 of the 3,6-anhydro-α-L-galactopyranosidic residues, and the total degree of sulfation (D.S.), that is the mean number of sulfate hemiester groups per monosaccharide unit, is always greater than 0.6;

(l) the contribution of sulfate hemiester groups, at position(s) 2 and 4 to the total degree of sulfation is always greater than 0.3.

The percentages under (a) are by weight. The percentages under (e) to (i) are molar percentages.

Preferably the ASP isolated from different sources have approximately a D.S. of $0.9 \pm 0.1$.

The agaroid skeleton of ASP may bear some out-of-chain galactose residues (up to 5%) as branch units, and up to 10% of the 4-0-linked α-L-galactopyranose residues may be replaced by 4-0-linked α-D-galactopyranose units.

Traces of xylose, which in the purified ASP does not exceed 5%, are frequently detected. If present, xylose occurs as branch units and may be eliminated by oxydation ($KIO_4$), followed by reduction ($NaBH_4$) and mild hydrolysis ($H^+$). The presence of xylose is not considered to be a distinctive feature, as the biological properties of ASP remain substantially unaffected in the presence or absence of this component.

ASP behaves as a relatively homogeneous chemical entity but is polydisperse, with a ratio $\overline{MW}/\overline{MN}$ usually greater than 2, and MP ranging 100 to 300 kDa.

$\overline{MW}$ means weight average molecular weight;
$\overline{MN}$ means number-average molecular weight; and
MP means molecular weight at peak maximum.

The ASP may be isolated starting directly from red algae to produce agarose, from residues of the manufacturing of agars (aqueous extracts) or, still in appreciable amounts, from general purpose commercial agars which have not been extensively purified.

Particularly preferred sulfated polysaccharides are carrageenan, heparin, dextran sulfate, pentosan polysulfate and ASP.

The sulfated polysaccharides of the invention are known compounds or may be obtained by known methods from known compounds or sources.

The ratio between the FGF component and the sulfated polysaccharide component in the compositions of the invention may vary widely, for example in general between 1:100 and 100:1. A ratio between 20:1 and 1:20 is preferable, particularly when the sulfated polysaccharide is carrageenan.

The antiviral activity of the pharmaceutical compositions of the invention has been generally tested, e.g., in vitro on Herpes simplex type 1 and type 2.

The tests were generally performed by resuspending monolayers of the permissive cells by tryptic treatment, and by seeding the suspensions ($10 \times 10^4$ cells/ml, in Minimal Essential Medium of Eagle supplemented with 5% inactivated Foetal Calf Serum) in 96 well flat bottom culture plates.

Samples of the product-compositions of the present invention in aqueous solution were distributed in two fold serial dilutions, in duplicate, into the wells added with cells and, after 15' of contact, infected with 100 $TCIC_{50}$ of virus/well. Points in the figures represent drug combinations necessary to reduce virus induced cytopatogenicity by 50% (CPE IV50) and numbers in parenthesis are FIC indexes.

Dose-response curves for both antiviral compounds alone and in combination were set up and the concentration of compound (sulfated polysaccharide or bFGF) required to reduce the cytopathic effect to 50% (CPE $ED_{50}$) of that in the control was calculated.

Data were plotted and analyzed by the isobologram method (Elion G. B. et al., J.Biol. Chem. 208, 477. 1954).

The fractional inhibitory concentration (FIC) for each pair, i.e., compound X plus compound Y, was calculated as follows:

$$FIC\ X = \frac{CPE\ IC_{50}\ \text{of the compound}\ X\ \text{in the combination}}{CPE\ IC_{50}\ \text{of compound}\ X\ \text{alone.}}$$

$$FIC\ Y = \frac{CPE\ IC_{50}\ \text{of the compound}\ Y\ \text{in the combination}}{CPE\ IC_{50}\ \text{of compound}\ Y\ \text{alone.}}$$

Combination resulting in additive antiviral [FIC X+FIC Y=1) are represented by straight lines (unity lines) on the isobolograms.

When the combination resulted in synergy (FIC X+FIC Y<1), the representational line shifts below the unity line.

When the combination resulted in antagonistic activity (FIC X+FIC Y>1), the line shifts above the unity line.

Points in the figures represent drug combinations necessary to reduce virus induced cytopatogenicity by 50% (CPE $IC_{50}$) and numbers in parenthesis are FIC indexes.

The in vitro effect of various combinations of λ carrageenan and bFGF (internal code FCE 26184) against HSV-1 are reported in FIG. 1.

The results obtained combining variable concentrations of λ carrageenan (from 1 to 0.015 mcg/ml) with constant concentrations of bFGF (100–50–25–12.5 nM) are represented by the lines — — — □ — — — and - - - - □- - - -.

The antiviral effect of variable concentrations of bFGF (from 200 to 3,12 nM) with constant concentrations of carrageenan (0.5–0.25–0.125–0.06 mcg/ml) are represented by the lines ———O——— and ..... O.
.....

In both cases a synergistic effect is obtained with the best synergism being shown by a combination containing 25 nM of bFGF and carrageenan at a concentration of 0.082 mcg/ml.

Figure 2:
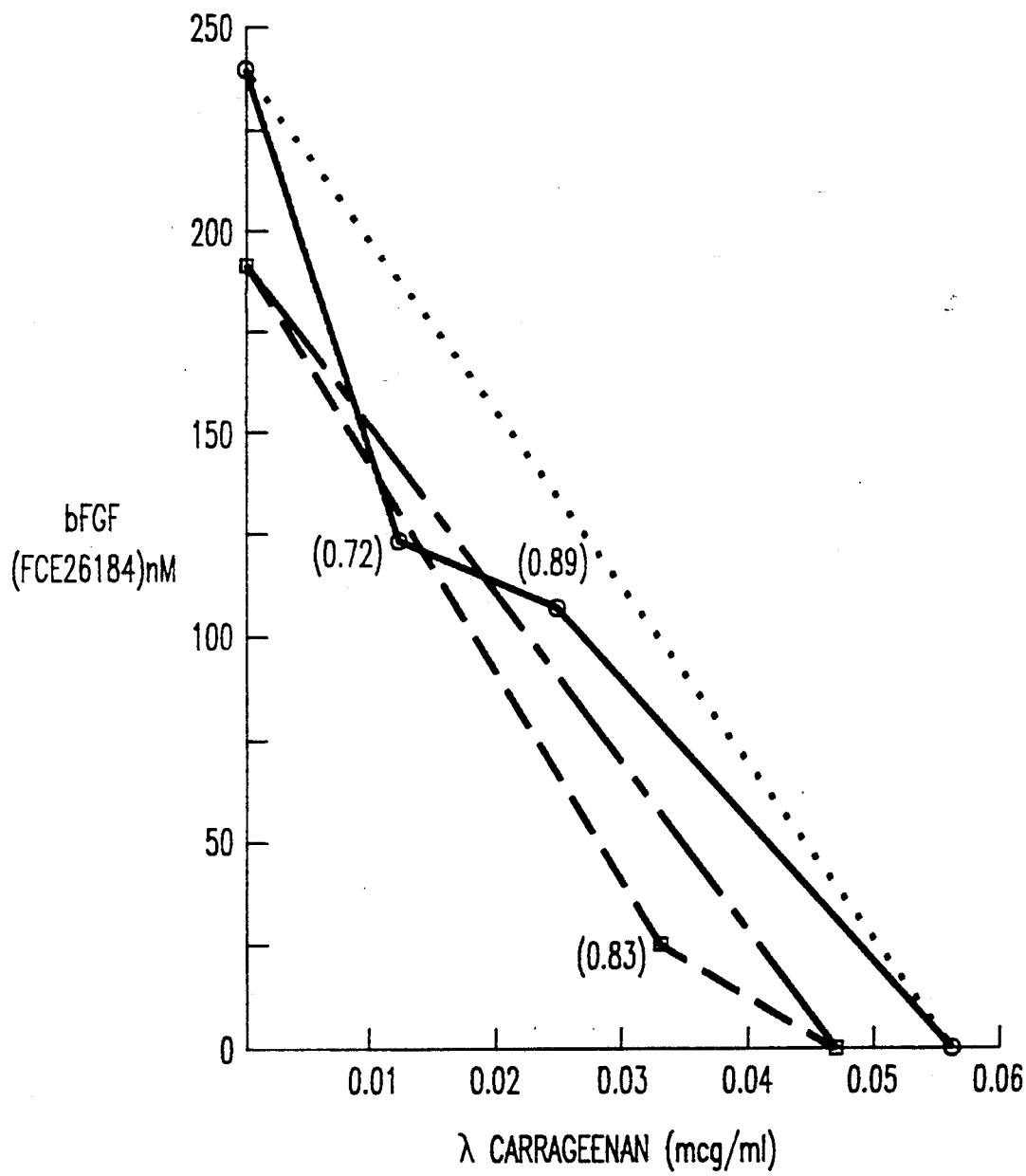
FIG. 2 shows the in vitro effect of various combination of $\lambda$ carrageenan and bFGF against HSV-2.

The in vitro effect of various combinations of λ carrageenan and bFGF (internal code FCE 26184) against HSV-2 are reported in FIG. 2.

The results obtained combining variable concentrations of λ carrageenan (from 0.2 to 0.003 mcg/ml) with constant concentrations of bFGF (100-50-25-12.5 nM) are represented by the lines — — — □— — — and - - - - - □- - - - -.

The antiviral effect of variable concentrations of bFGF (from 200 to 3.12 nM) with constant concentrations of λ carrageenan (0.1-0.05-0.025-0.0125 mcg/ml) are represented by the lines ———O——— and ..... O......

In both cases a synergistic effect is obtained, with the best combination being constituted by a combination containing 123.5 nM of bFGF and 0.0125 mcg/ml of λ carrageenan.

Figure 3:
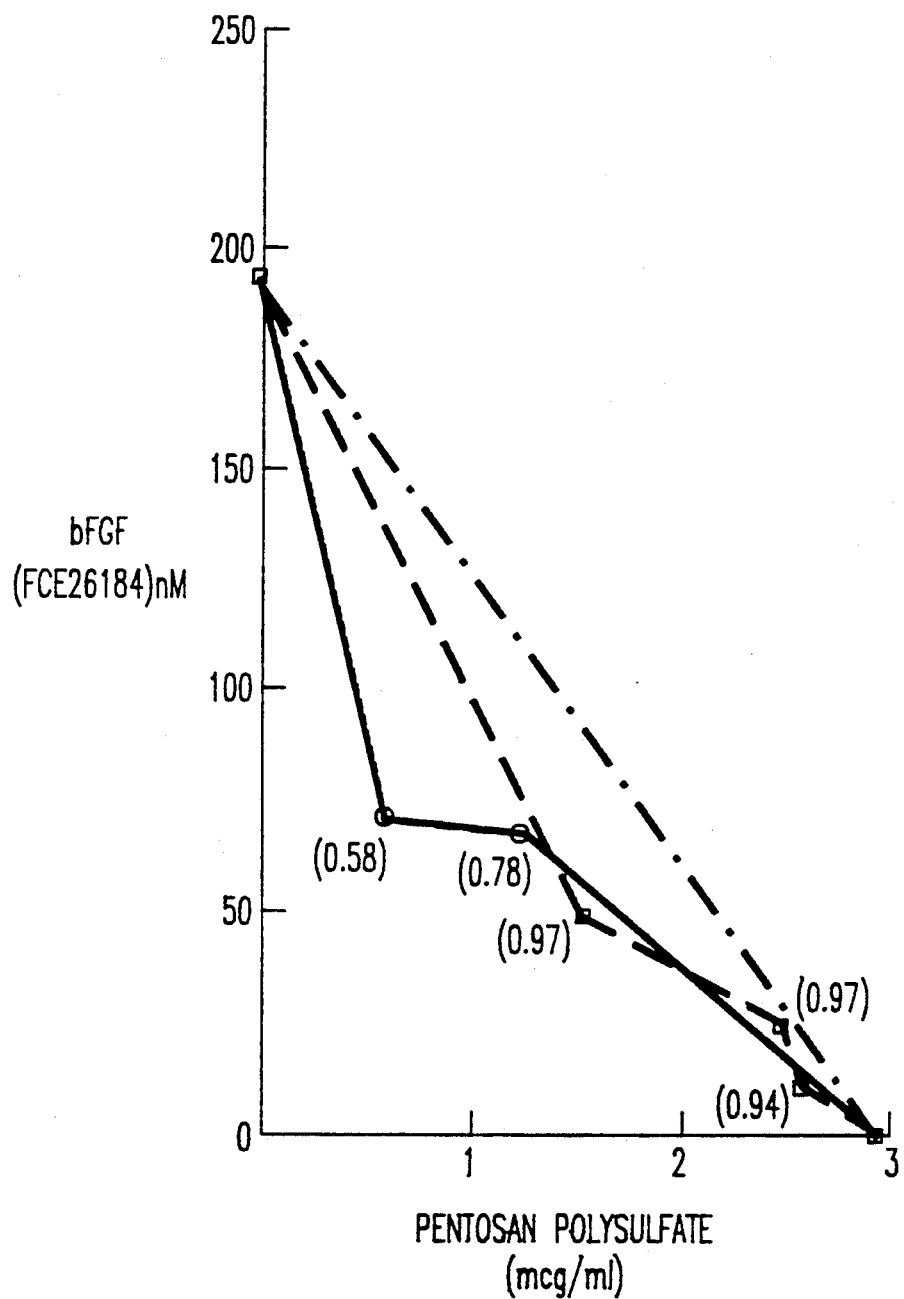
FIG. 3 shows the in vitro effect of various combinations of $\lambda$ pentosan polysulfated and bFGF against HSV-1.

The in vitro effect of various combinations of pentosan polysulfated and bFGF (internal code FCE 26184) against HSV-1 is reported in FIG. 3.

The results obtained combining variable concentrations of pentosan polysulfate (from 10 to 0.15 mcg/ml) with constant concentration of bFGF (100-50-25-12.5 nM) are represented by the lines ———□——— and —. —. —□—. —. —.

The antiviral effect of variable concentrations of bFGF (from 200 to 3.12 nM) with constant concentrations of pentosan polysulfate (5-2.5-1.25-0.6 mcg/ml) is represented by the lines ———O———and —. —. —□—. —. —.

In both cases a synergistic effect is obtained with the best synergism being shown by a combination containing 71.4 nM of bFGF and pentosan polysulphate at a concentration of 0.6 mcg/ml.

Figure 4:
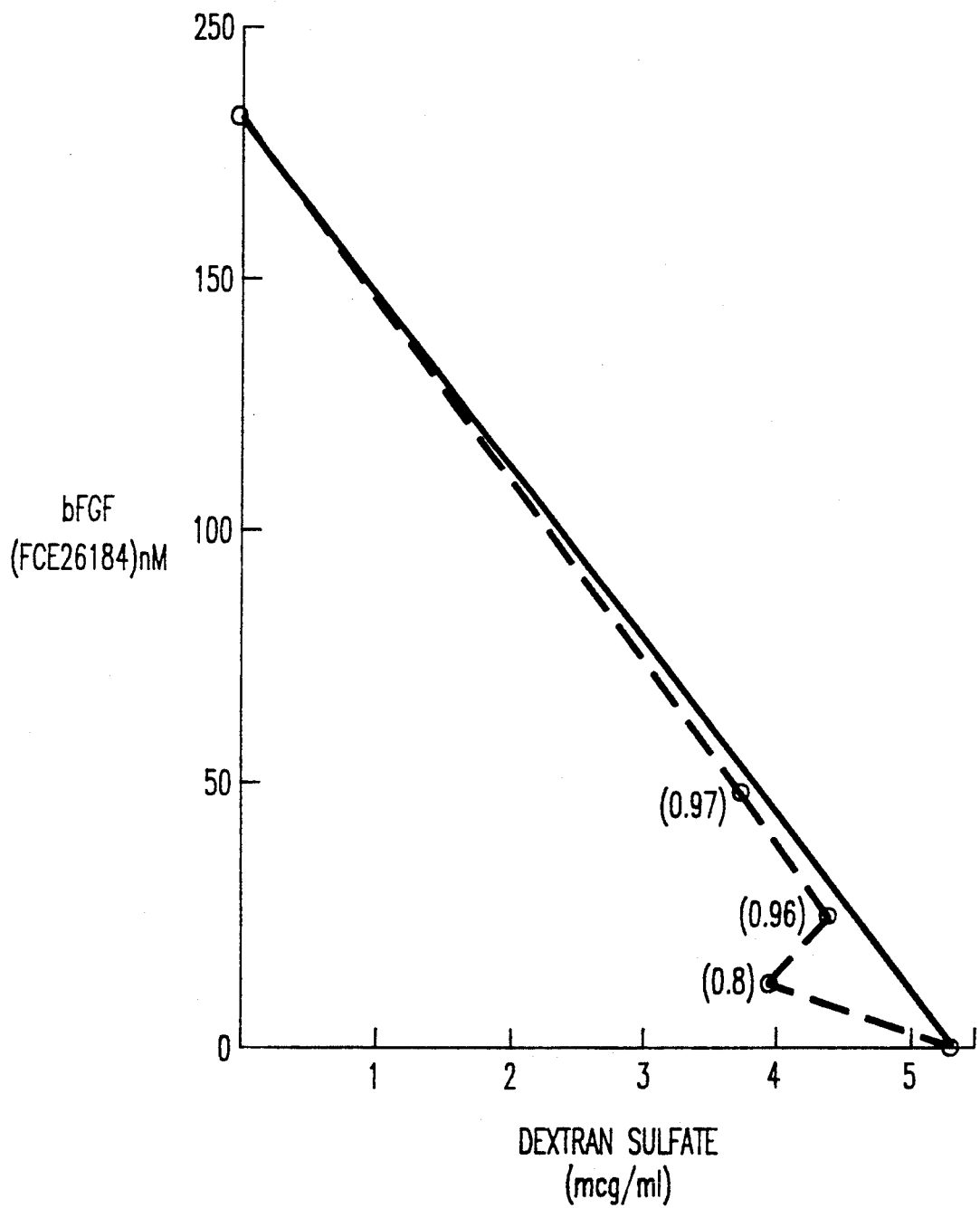
FIG. 4 shows the in vitro effect of various combinations of dextran sulfate and bFGF against HSV-1.

The in vitro effect of various combination of dextran sulfate (M.W. 8000) and bFGF (internal code FCE 26184) against HSV-1 is reported in FIG. 4.

The results obtained combining variable concentrations of dextran sulfate (from 10 to 0.15 mcg/ml) with constant concentrations of bFGF (100-50-25-12.5 nM), represented by the lines ———O——— and ..... O. ...., indicate that a synergistic effect is obtained. The maximum effect is reached combining 12.5 nM of bFGF and 3.9 mcg/ml of dextran sulfate.

Figure 5:
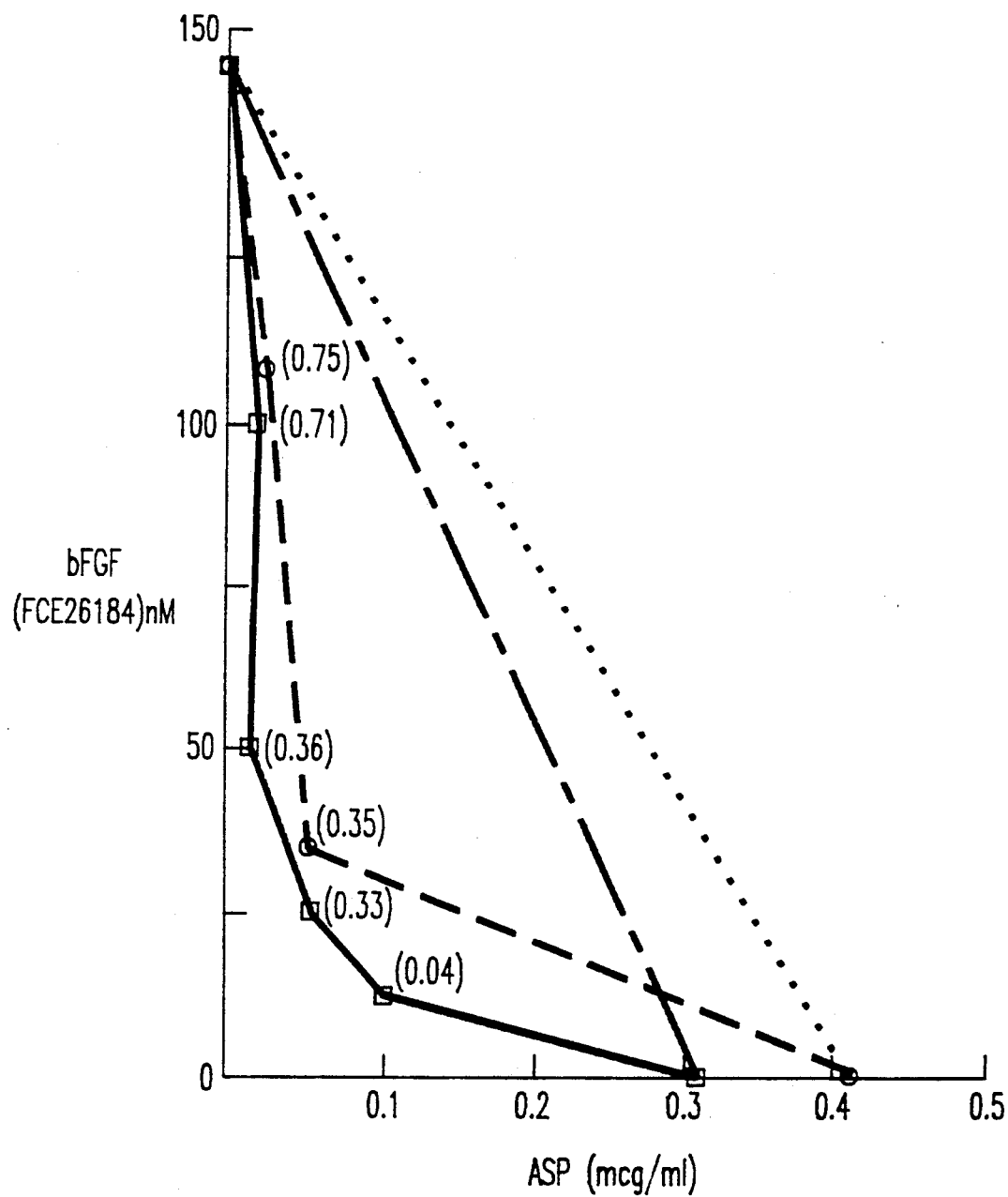
FIG. 5 shows the in vitro effect of various combinations of the sulfate polysaccharides ASP and bFGF against HSV-1.

The in vitro effect of various combinations of the sulfated polysaccharides ASP (lot 8682/54) and bFGF against HSV-1 is reported in FIG. 5.

The results obtained combining variable combinations of ASP (lot 8682/54) (from 0.8 to 0.125 mcg/ml) with constant concentrations of bFGF (100-50-25-12.5 nm) are represented by the lines ———□——— and - - - - - □- - - - -.

The antiviral effect of variable concentrations of bFGF (from 200 to 3.12 nM) with constant concentrations of ASP (lot 8682/54) (0.2-0.1-0.05-0.025) is represented by the lines — — — O— — — and ..... O. . ...

Figure 6:
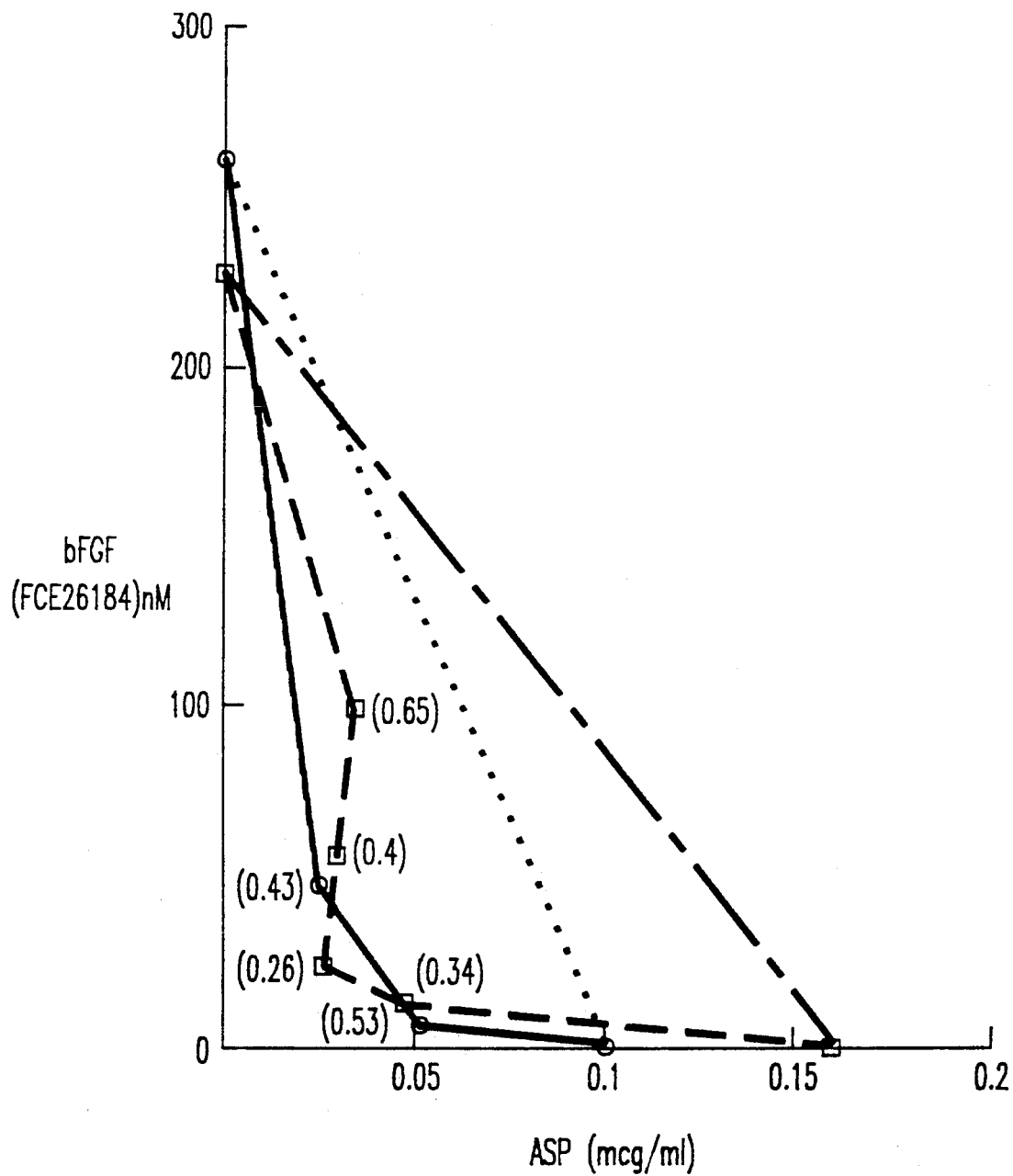
FIG. 6 shows the in vitro effect of various combinations of ASP and bFGF against HSV-2.

In both cases a synergistic effect is obtained, with the best combination being constituted by a combination containing 25-50 nM of bFGF and 0,0125-0.05 mcg/ml of ASP (lot 8682/54). The in vitro effect of various combinations of ASP (lot 8682/54) and bFGF against HSV-2 is reported in FIG. 6.

The results obtained combining variable concentrations of ASP (lot 8682/54) (from 0.8 to 0.0125 mcg/ml) with constant concentrations of bFGF (100-50-25-12.5 nM) are represented by the lines and — — — — □— — — — and - - - - - □- - - - -.

The antiviral effect of variable concentrations of bFGF (from 200 to 3.12 nM) with constant concentrations of ASP (lot 8682/54) 0.2-0.1-0.05-0.025 mcg/ml) is represented by the lines ———O——— and ... .. O. ....

In both cases a synergistic effect is obtained, with the best effect being constituted by a combination containing 12.5-25 nM of bFGF and 0.026-0.047 mcg/ml of ASP (lot 8682/54). With reference to the FIGS. 1 to 6, the bFGF (FCE 26184) whose preparation is described in the experimental section hereinbelow, represents a human bFGF of 153-154 aminoacids, precisely an approximately 50:50 mixture of a) a 153 aminoacid molecule having the sequence of 146 aminoacids shown previously for human bFGF (SEQ ID NO:1) and a N-terminal extension of 7 aminoacids (SEQ ID NO:5) (SEQ ID NO:4), and b) a 154 aminoacid molecule having the sequence of 146 aminoacids shown previously for human bFGF (SEQ ID NO:1) and a N-terminal extension of 8 aminoacids (SEQ ID NO:4) (SEQ ID NO:5).

Similar results could be obtained also with other bFGF forms, e.g. the human bFGF 146 aminoacid form depicted by (SEQ ID NO:1).

The pharmaceutical compositions of the invention may comprise one or more of the said growth factors, one or more of the said sulfated polysaccharides, as such or as pharmaceutically acceptable salt thereof, and one or more pharmaceutical acceptable excipients.

Examples of pharmaceutically acceptable salts of the fibroblast growth factors of the invention can be the salts with pharmaceutically acceptable inorganic acids for example hydrochloric, hydrobromic, sulphuric and phosphoric acid, and salts with pharmaceutically acceptable organic acids, e.g. acetic, citric, maleic, malic, succinic, ascorbic and tartaric acid.

Examples of pharmaceutically acceptable salts of the sulfate polysaccharides of the invention can be salts with pharmaceutically acceptable inorganic bases, for example alkali metal hydroxides such as sodium or potassium hydroxide or alkaline earth metal hydroxides, such as calcium hydroxide.

The two components of the composition may be combined in any suitable way. Although it is possible to provide the combination as a two-component system, it is preferable to produce a one-component system in which both components are combined with each other in a common excipient.

The excipient may be any medium which is conventional or suitable for this purpose.

The compositions of the invention can be administered, for example, by the topical, parenteral, intravenous, intrathecal or oral route.

One particularly preferred route of administration is the topical route which is used, for example, in the treatment of skin and/or eye infections caused by HSV1 virus or of genital infections caused, e.g., by HSV2, or of respiratory infections caused by HRSV.

Compositions suitable for topical administration can be for example, creams, pastes, ointments or lotions for dermatological treatment; suppositories or pessaries for the treatment of vaginal infections; collyrium for the treatment of ocular infections; or aerosols for the treatment of infections of the respiratory system, especially, for example, for treating HRSV infections in newborn babies.

These formulations can be prepared according to known techniques; for example, creams, pastes, ointments and lotions can be obtained by mixing the active principle with conventional oleaginous or emulsifying excipients. Compositions suitable for intravenous or intrathecal administration can be, for example, sterile aqueous solutions or sterile isotonic physiological saline solutions. Compositions suitable for parenteral administration can be, for example, suspensions or solutions containing the active principle and a pharmaceutically acceptable carrier as such, for example, sterile water, olive oil, glycols, for example propylenic glycols and, if desired, an appropriate quantity of lidocaine hydrochloride.

Formulations suitable for oral administration can be, e.g., tablets or capsules coated with a gastro- and enteroresistant-layer, in which the active principle can be mixed, for example, with diluents, e.g., lactose, dextrose and the like; lubricants, e.g., silica, talcum, stearic acid and the like; binders, e.g., starch; disaggregants, e.g., alginic acid and alginates; and other excipients commonly used for this type of formulation.

In general, the pharmaceutical compositions according to the invention can be prepared with known techniques and according to procedures commonly used in the field of galenic preparations.

The beneficial dose depends upon the pathological condition to be treated, the type of formulation used, the condition of the patient and the length of the treatment. Formulations suitable for topical administration can be, for example, creams, pastes, ointments, lotions, vaginal pessaries, suppositories and collyriums.

The following examples show non-restrictive methods for preparing the FGF growth factors and the analogues thereof according to the invention.

EXAMPLE 1

Preparation of b-FGF (FCE 26184)

The construction of synthetic DNA sequence for b-FGF and of the expression plasmid carrying such sequence was performed according to the procedure described in EP-A-363675. The fermentation and purification process was carried out as follows:

a) Fermentation process

A bacterial strain, *E.coli* type B, from the Institute Pasteur collection, was transformed with a plasmid carrying both the human gene coding for b-FGF and the gene for tetracycline resistance. This transformed strain was used for the production of recombinant non-glycosylated h-b-FGF (human b-FGF). A Master Cell Bank (15 freeze-dried vials) and a Working Cell Bank (W.C.B.) (70 vials stored in liquid nitrogen at −190° C.) of this strain were prepared. The content of one vial of W.C.B. was used as the inoculum for the fermentation phase.

The fermentation process was carried out in 10 l fermentors filled with 4 l of culture medium.

Tetracycline hydrochloride was added to the medium in order to maintain the conditions of strain selection.

After 20 hours of growth at 37° C. the final biomass was 42±2 g/l dry weight, an the production of b-FGF was 2500±500 mg/l as measured by comparative gel electrophoresis.

Enrichment in pure oxygen was required during the fermentation phase in order to allow a large bacterial growth.

(b) Initial purification

The cells (microorganisms) were separated from the total fermentation broth by centrifugation. The resulting pellet was resuspended in a sodium phosphate buffer containing sodium chloride. A minimum of 3 passages through a high pressure homogenizer were necessary for efficient cell breakage. The resulting cell lysate was clarified by centrifugation and the supernatant was collected for further processing.

(c) Purification

The clarified supernatant was loaded on a column of Sepharose (Trade Mark) S Fast Flow (cation exchanger) and the product was eluted from this column using a gradient of increasing sodium chloride concentrations in a phosphate buffer (Trade Mark). The product was further purified on a column of Heparin Sepharose 6 B by eluting with a gradient on increasing sodium chloride concentration in a phosphate buffer. Finally a buffer exchange was made on a Sephadex (Trade Mark) G25 resin to obtain the product in the bulk product buffer (sodium phosphate -EDTA).

(d) Column sanitization

Sepharose S Fast Flow and Sephadex G25 columns were sanitized by washing with sodium hydroxide solutions. Heparin Sepharose was washed alternatively with solutions at pH=8.5 and pH=5.5 containing 3M sodium chloride.

EXAMPLE 2

Preparation of b-FGF fragments.

The synthesis of fragment 93-120 of bFGF with the formula (SEQ ID NO:8): H-Phe-Phe-Phe-Glu-Arg-Leu-Glu-Ser-Asn-Asn-Tyr-Asn-Thr-Tyr-Ar-g-Ser-Arg-Lys-Tyr-Ser-Ser-Trp-Tyr-Val-Ala-Leu-Lys-Arg-NH₂ was carried out in consecutive stages using a peptide synthesizer and MBHA resin. The bond to the resin was obtained via BOC-Val according to the procedures described in the U.S. Pat. No. 4,292,313. After bonding to the resin the amino protective group was removed for treatment with trifluoroacetic acid at 0° C. After deprotection and subsequent neutralization, the peptide chain was constructed step by step on the resin following the procedure described in the U.S. Pat. No. 3,904,594.

A similar method can be used to prepare the following peptides:

1) fragment 97-120 of bFGF with the formula (SEQ ID NO: 9):
H—Arg—Leu—Glu—Ser—Asn—Asn—Tyr—Asn—Thr—Tyr—Arg—Ser—Arg—Lys—
—Tyr—Ser—Ser—Trp—Tyr—Val—Ala—Leu—Lys—Arg—NH₂;
2) fragment 100-120 of bFGF with the formula (SEQ ID NO: 10):
H—Ser—Asn—Asn—Tyr—Asn—Thr—Tyr—Tyr—Arg—Ser—Arg—Lys—Tyr—Ser—
—Ser—Trp—Tyr—Val—Ala—Leu—Lys—Arg—NH₂;
3) fragment 103-120 with the formula (SEQ ID NO: 11):

-continued

H—Tyr—Asn—Thr—Tyr—Arg—Ser—Arg—Lys—Tyr—Ser—Ser—Trp—Tyr—Val—
—Ala—Leu—Lys—Arg—NH$_2$;

4) fragment 103-106 with the formula (SEQ ID NO: 12):
H—Tyr—Asn—Thr—Tyr—Arg—Ser—Arg—Lys—Tyr—Ser—Ser—Trp—Tyr—Val—
—Ala—Leu—Lys—Arg—Thr—Gly—Gln—Tyr—Lys—Leu—Gly—Pro—Lys—Thr—
—Gly—Pro—Gly—Gln—Lys—Ala—Ile—Leu—Phe—Leu—Pro—Met—Ser—Ala—
—Lys—Ser—NH$_2$;

5) fragment 106-115 with the formula (SEQ ID NO: 13):
H—Tyr—Arg—Ser—Arg—Lys—Tyr—Ser—Ser—Trp—Tyr—NH$_2$;

6) fragment 106-118 with the formula (SEQ ID NO: 14):
H—Tyr—Arg—Ser—Arg—Lys—Tyr—Ser—Ser—Trp—Tyr—Val—Ala—Leu—
—NH$_2$;

7) fragment 106-120 with the formula (SEQ ID NO: 15):
H—Tyr—Arg—Ser—Arg—Lys—Tyr—Ser—Ser—Trp—Tyr—Val—Ala—Leu—Lys—
—Arg—NH$_2$;

8) amidated fragment 106-125 of bFGF;
9) amidated fragment 106-130 of bFGF;
10) amidated fragment 106-135 of bFGF;
11) amidated fragment 106-140 of bFGF;
12) amidated fragment 106-146 of bFGF;
13) amidated fragment 107-110 of bFGF.

EXAMPLE 3

Extraction and Purification of ASP (lot 8682/54)

454 g of Bacto-Agar (TM) Difco were suspended in 6 l of aqueous 0.5M NaCl, containing 2 mM sodium azide, and vigorously stirred for 2 h at room temperature. The aqueous extract (4400 ml) obtained by filtering through glass wool, was added of 37 ml of 5M NaCl, 24 ml of 2M sodium sulphate, and 330 ml of a 6% (w/v) aqueous solution of cetyltrimethyl-ammonium bromide (CTAB), under stirring, while slightly warmed (40° C.) for 30 min. and allowed to aggregate while standing for at least 2 h at room temperature. The presence of 0.5 Ml NaCl prevented pectins and low charge density sulphated polysaccharides (D.S.<0.3) from precipitating.

The precipitate was collected by brief centrifugation and dissolved in 640 ml of 4M NaCl while stirring at 40° C. overnight. The residual agarose and insoluble impurities were centrifuged off.

Sodium sulphate (14 ml, 2M) CTAB (46 ml, 6%) and 2040 ml of water were sequentially and slowly added to the clear supernatant (700 ml, from re-dissolution in 4M NaCl) with good mixing, lowering the sodium chloride concentration down to 1M, and promoting an homogeneous precipitation. After warming (40° C., 30 min.) with stirring and standing ($\geq 2$ h) at room temperature, the precipitate, which centrifuges upward, was collected and re-dissolved in 300 ml of 4M NaCl (40° C., with stirring, overnight).

Methanol (1685 ml) was added slowly, with adequate stirring, to the clear solution (315 ml) to precipitate sulphated polysaccharides as their sodium salts, leaving all CTAB and most NaCl in the supernatant (2000 ml, 84% MeOH). Stirring was maintained for at least 2 h, when ion exchange proceeded to completion.

The precipitate was collected by filtration, dissolved in 150 ml of water (tot. vol.180 ml), completely clarified by filtration (0.45 μm) and precipitated again in 84% MeOH (by addition of 1000 ml MeOH) to remove all NaCl. Final washes with 95% MeOH (350 ml twice) and 100% MeOH (300 ml) and drying afforded the purified sodium salts of sulphated polysaccharides having a D.S.$\geq$0.6 in 1.0% yield (4.4 g, lot 8682/54, D.S.=0.85).

---

We claim:

1. A pharmaceutical composition, comprising an amount of:
   (i) a fibroblast growth factor selected from the group consisting of an amidated human or bovine fibroblast growth factor, a human or bovine fibroblast growth factor having an N-terminal extension selected from the group consisting of SEQ ID NOS:2, 3, 4 and 5, an amidated human or bovine fibroblast growth factor having an N-terminal extension selected from the group consisting of SEQ ID NOS:2, 3, 4 and 5, the peptides of SEQ ID NOS:8, 9, 10, 11, 12, 13, 14 and 15, amidated peptides of SEQ ID NOS:8, 9, 10, 11, 12, 13, 14 and 15, and mixtures thereof;
   (ii) a sulfated polysaccharide having antiviral activity; and
   (iii) a pharmaceutically acceptable excipient, effective for the treatment or prevention of infections caused by enveloped viruses.

2. The pharmaceutical composition of claim 1, wherein said fibroblast growth factor is selected from the group consisting of peptides of SEQ ID NOS:8, 9, 10, 11, 12, 13, 14 and 15, and amides thereof.

3. A pharmaceutical composition, comprising an amount of:
   (i) a fibroblast growth factor,
   (ii) carrageenan, pentosan polysulfate, dextran polysulfate, a sulfated polysaccharide produced by marine algae of the class Rhodopyceae, or a mixture thereof, and
   (iii) a pharmaceutically acceptable excipient, effective for the treatment or prevention of infections caused by enveloped viruses.

4. The pharmaceutical composition of claim 3, wherein said sulfated polysaccharide is composed of alternating $\beta$-(1→4)D-galactose and $\alpha$-(1→3)L-galactose units.

5. A method of preventing or treating an infection caused by an enveloped virus, comprising administering to a patient in need thereof an effective amount of the composition of claim 1 or 3.

6. The pharmaceutical composition of claim 3, wherein said fibroblast growth factor is selected from the group consisting of:
   (a) H-Phe Phe Phe Glu Arg Leu Glu Ser Asn Asn Tyr Asn Thr Tyr Arg Ser Arg Lys Tyr Ser Ser Trp Tyr Val Ala Leu Lys Arg-NH$_2$ (SEQ ID NO:8),
   (b) H-Arg Leu Glu Ser Asn Asn Tyr Asn Thr Tyr Arg Ser Arg Lys Tyr Ser Ser Trp Tyr Val Ala Leu Lys Arg-NH$_2$ (SEQ ID NO:9),
   (c) H-Ser Asn Asn Tyr Asn Thr Tyr Tyr Arg Ser Arg Lys Tyr Ser Ser Trp Tyr Val Ala Leu Lys Arg-NH$_2$ (SEQ ID NO:10),
   (d) H-Tyr Asn Thr Tyr Arg Ser Arg Lys Tyr Ser Ser Trp Tyr Val Ala Leu Lys Arg-NH$_2$ (SEQ ID NO:11),
   (e) H-Tyr Asn Thr Tyr Arg Ser Arg Lys Tyr Ser Ser Trp Tyr Val Ala Leu Lys Arg Thr Gly Gln Tyr Lys Leu Gly Pro Lys Thr Gly Pro Gly Gln Lys Ala Ile Leu Phe Leu Pro Met Ser Ala Lys Ser-NH$_2$ (SEQ ID NO:12),
   (f) H-Tyr Arg Ser Arg Lys Tyr Ser Ser Trp Tyr-NH$_2$ (SEQ ID NO:13),
   (g) H-Tyr Arg Ser Arg Lys Tyr Ser Ser Trp Tyr Val Ala Leu-NH$_2$ (SEQ ID NO:14), and
   (h) H-Tyr Arg Ser Arg Lys Tyr Ser Ser Trp Tyr Val Ala Leu Lys Arg-NH$_2$ (SEQ ID NO:15).

7. The pharmaceutical composition of claim 3, wherein said fibroblast growth factor is a basic fibroblast growth factor.

8. The pharmaceutical composition of claim 7, wherein said fibroblast growth factor is a mixture of human basic fibroblast growth factor (SEQ ID NO:1) having an N-terminal extension of SEQ ID NO:4 and human basic fibroblast growth factor (SEQ ID NO:1) having an N-terminal extension of SEQ ID NO:5.

9. A pharmaceutical composition according to claim 3 wherein the fibroblast growth factor is basic fibroblast growth factor (b-FGF), or an analogue thereof.

10. A pharmaceutical composition according to claim 1 wherein the sulfated polysaccharide with antiviral activity is selected from the group consisting of a carrageenan, heparin, dextran sulfate, pentosan polysulfate, mannan sulfate, dermatan sulfate, heparin super-sulfated, dermatan supersulfated and an agarose-type sulfated polysaccharide produced by marine algae belonging to the class of Rhodophyceae (ASP).

11. A pharmaceutical composition according to claim 10 wherein the sulfated polysaccharide is selected from the group consisting of carragenan, heparin, dextran sulfate, pentosan polysulfate and an agarose-type sulfated polysaccharide produced by marine algae belonging to the class of Rhodophyceae (ASP).

12. A method according to claim 5 wherein the virus is a herpes virus type $\alpha$, $\beta$ or $\gamma$; an orthomyxovirus or paramyxovirus; a tropical virus or a retrovirus.

13. A method according to claim 12 wherein the herpes virus type $\alpha$ is herpes simplex virus (HSV) or herpes varicella/zoster; the herpes virus type $\beta$ or $\gamma$ is a cytomegalovirus; the orthomyxovirus is an influenza virus; the paramyxovirus is the human respiratory syncytial virus (HRSV); the tropical virus is the Semliki Forest virus (SFV); the retrovirus is the Human Immunodeficiency virus (HIV) or the Moloney Sarcoma virus (MSV).

14. A method according to claim 13 wherein the herpes simplex virus is the virus HSV-1 or HSV-2.

* * * * *